United States Patent [19]

Tucker

[11] Patent Number: 5,348,006
[45] Date of Patent: Sep. 20, 1994

[54] HEAD SENSOR POSITIONING PEDESTAL

[75] Inventor: Don M. Tucker, Eugene, Oreg.

[73] Assignee: Electrical Geodesics, Inc., Eugene, Oreg.

[21] Appl. No.: 750,108

[22] Filed: Aug. 26, 1991

[51] Int. Cl.$^5$ ............................................. A61B 5/0478
[52] U.S. Cl. ..................................... 128/639; 128/644
[58] Field of Search ............... 128/639, 644, 791, 802, 128/803; 607/139, 149, 153

[56] References Cited

U.S. PATENT DOCUMENTS

| | | |
|---|---|---|
| 3,490,439 | 1/1970 | Rolston . |
| 3,508,541 | 2/1970 | Westbrook et al. . |
| 3,735,753 | 5/1973 | Pisarski . |
| 3,998,213 | 12/1976 | Price . |
| 4,033,334 | 7/1977 | Fletcher et al. . |
| 4,085,739 | 4/1978 | Sams . |
| 4,202,344 | 5/1980 | Mills et al. ........................... 128/644 |
| 4,308,873 | 1/1982 | Maynard . |
| 4,323,076 | 4/1982 | Sams . |
| 4,537,198 | 8/1985 | Corbett . |
| 4,709,702 | 12/1987 | Sherwin . |

FOREIGN PATENT DOCUMENTS

| | | | |
|---|---|---|---|
| 3527474 | 6/1986 | Fed. Rep. of Germany | 128/639 |
| 198502 | 5/1976 | U.S.S.R. | 128/639 |

Primary Examiner—Lee S. Cohen

[57] ABSTRACT

A device for holding a measurement sensor perpendicular to the human head in which the sensor, such as a sponge EEG electrode, is incorporated within a pedestal tube (14) attached to a perpendicular pedestal collar (15) which is in turn attached to and positioned by a holding device, such as a the sensor positioning tension network (16) of my related invention, or an elastic cap. The distance of the pedestal collar, and thus the holding device, from the head can be adjusted, such as with a lock ring (17), such that only the foot of the sensor pedestal (18) enters the hair. The flared shape of the foot of the sensor pedestal acts to part and lift the hair during application, allowing the sensor pedestal tube, and in this embodiment the sponge of the EEG electrode (13), to rest directly on the scalp.

2 Claims, 1 Drawing Sheet

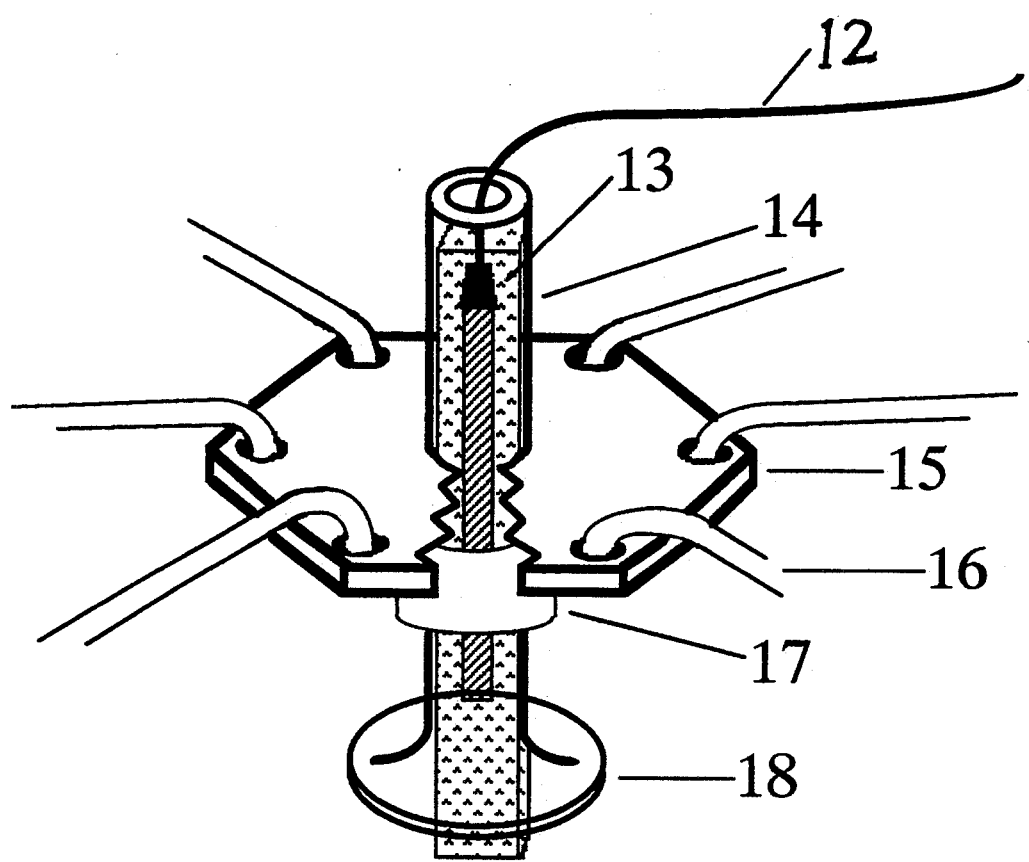

HEAD SENSOR POSITIONING PEDESTAL

FIELD OF THE INVENTION

This invention is within the field of medical and scientific instruments, in which sensors for measuring the brain's anatomy or function are applied to the head. The specific application of the preferred embodiment is electroencephalographic (EEG) recording of the brain's electrical fields, in which the sensors are electrodes contacting the scalp surface.

CROSS-REFERENCE TO RELATED APPLICATIONS

This application is related to my U.S. patent application submitted concurrently entitled "Head Sensor Positioning Network." The head sensor positioning pedestal rests on the scalp directly, allowing the positioning network of my related application to be suspended above the hair, thus achieving a comfortable and secure attachment of an array of sensors to the human head.

DESCRIPTION OF PRIOR ART

A frequent objective of new inventions has been a holding device for attaching scalp EEG electrodes in a way that is both comfortable for the wearer and conformable to the various shapes taken by human heads. In several examples of the prior art, elastic straps or material have been used to adjust the positioning of the electrodes (U.S. Pat. No. 3,490,439 to Rolston, 1970; U.S. Pat. No. 3,998,213, to Price, 1976; U.S. Pat. No. 4,709,702 to Sherwin, 1987; U.S. Pat. No. 4,537,198 to Corbett; 1985). In my concurrent application, a holding device is comprised of a network of elastic lines arranged among the electrode sensors in an explicit, geodesic geometry, thereby providing a systematic method for conforming the positioning of the sensors to individual head geometries.

A problem common to each of these methods is that when the friction of the apparatus is applied against the hair, the hair slides easily, degrading the friction purchase of the holding device on the head, thus causing its positioning and attachment to be unstable. The poor friction of holding devices that rely on elastic straps or caps is countered either by increasing their tension, thereby risking the subject's discomfort, or by adding chin, chest, or arm straps (see also U.S. Pat. No. 4,085,739 to Sams, 1978), thereby applying new lines of tension that distort the even conformation of the elastic structure of the holding device to the subject's head.

Another problem with previous designs has been that an elastic method that conforms to differing head shapes also compresses the hair around the electrode site, causing the hair to interfere with the electrode-to-scalp interface. This interference is particularly detrimental to sponge EEG electrodes, for which a liquid electrolyte forms the conductance path between the scalp and the electrode. The hair not only increases the resistance between electrode and scalp. If a significant number of hair strands contact the sponge surface, they wick away the electrolyte solution. Given the relatively high temperature of the scalp itself, this can result in a dry and non-functional electrode in a few minutes. This problem has been addressed by Westbrook et al (U.S. Pat. No. 3,508,541, 1970) by sealing the sides of the sponge, such as with silicone. But unless there is a method for positioning the sponge under the hair and directly on the scalp surface, the bottom of the sponge will usually sit on a mat of hair, causing the electrical connection to be poor and short-lived.

Because of these problems with hair, sponge electrodes are now seldom used in research or in clinical practice. For non-sponge electrodes, the problem of the hair is typically handled by paying individual attention to each electrode, such as by parting the hair at each location where the electrode is glued. For the cap design now commercially available, the application procedure involves inserting a blunt syringe through a hole in the electrode, parting the hair, scraping the epidermis from the scalp surface, then injecting a thick electrolyte paste to make an electrical connection between the electrode and the scalp surface.

A thick paste is less susceptible to being wicked away by the hair than the liquid saline or other electrolytes used with sponges. Yet if paste were used with each electrode of a dense array of, for example, 128 electrodes, the subject would be left with a head fully covered by this rather unattractive material.

Furthermore, although skilled EEG technicians are usually able to minimize the lesions caused by scraping the scalp, any abrasions can be painful for persons with sensitive skin. More importantly, the subject who is feeling these lesions often becomes concerned about the risk of HIV or other viral infection. Although sterile procedures can certainly be followed, many patients or experimental subjects are now fearful of the disease risk caused when even minor skin abrasions are inflicted.

Both theoretical computations and the initial evidence on volume conduction of electrical fields through the skull indicate that at least 128 scalp electrodes would be required to provide adequate spatial sampling of the scalp electrical fields for the human head. In a recent study in a well-known EEG research laboratory, applying this many electrodes with a conventional non-sponge method required four technicians working on the subject for two hours. At the end of this application, with over one hundred small scalp abrasions, only the most hardly and enthusiastic subject is ready to begin a medical test or scientific experiment.

OBJECTS AND ADVANTAGES

The main object of this invention is to position a head sensor (such as an EEG electrode) against the scalp while raising the holding device that applies pressure to that sensor (such as a strap, elastic cap, or the geodesic tension network of my related patent application) sufficiently away from the scalp that it does not compress the hair. The sensor positioning pedestal would thus avoid the hair as it communicates the pressure of the holding device to the scalp, while simultaneously communicating its friction against the scalp back to the holding device.

A related object of the invention is to achieve a method for inserting the sensor through and under the hair, directly against the scalp, such that efficient placement of an organized array of sensors can be accomplished without individual attention to each one.

To achieve these objects, I have invented a head sensor positioning pedestal. The preferred embodiment of this invention is integrated within the head sensor positioning tension network of my related application, and its advantages will be described within that embodiment. But the advantages of this invention can also be seen to accrue to other holding device embodiments, such as those using an elastic cap or straps to hold sensors against the head.

The sensor positioning pedestal incorporates the sensor (which is a sponge EEG electrode in the preferred embodiment) within a plastic tube, such that the sponge protrudes from the scalp end (foot) of the tube. At an adjustable distance away from the scalp, a collar attaches the sensor pedestal to the elastic tension structure network, thus raising this holding device above the hair.

The specific advantage of the collar is an important feature of the invention, allowing it to raise the holding device above the hair, while keeping the pedestal perpendicular to the plane of the holding device (and thus in line with the radius extending to the scalp contact point from the approximate center of the head). In the embodiment with the head sensor positioning network, a balanced tension is created by the network of geodesic triangles partitioning the spherical surface of this holding device. This surface tension in a spherical configuration results in radial force vectors from each geodesic vertex toward the sphere center. It can be seen that if the vertex shifts somewhat, such as from a head movement, a new radial force vector is applied from the new vertex location, and if this new vector is applied against a now tilted sensor pedestal, the structure collapses about the subject's head in an unseemly tangle of thread, wire, plastic parts, and wet sponges.

This problem is solved by adding to the sensor pedestal the collar oriented in the plane of the geodesic surface that causes any deviation of the pedestal from the radial orientation to disrupt the surface tension of the elastic lines, and thus be counteracted by that surface tension. This design thus provides the advantages of (1) keeping the sensor pedestals upright (oriented head-radially), and (2) simultaneously keeping the net from shifting parallel to the head surface.

Given the structural stability afforded to the elastic holding device, only the sensor pedestals themselves need enter into the hair. This is clearly useful when the sensors are EEG electrodes, but it may be an advantage for any sensor system. Placed under the hair, each sensor pedestal gains a friction purchase on the scalp, holding the network in place comfortably.

This advantage was optimized by designing the sensor pedestals to insert their feet under the hair as the holding device (the head sensor positioning network or "net") is applied. The foot, or scalp end, of the sensor pedestal is flared. As the net is placed on the head, it is moved back and forth slightly, during which time the radial compression on the sensor pedestal is slight but continuous, such that the flare on the pedestal foot not only parts but rakes and lifts up the hair strands it contacts, inserting itself below them. After a few movements, the foot rests directly on the scalp, overlying only those few hairs whose pores are directly below it. As the net is applied to the head, slight back-and-forth movements cause this hair-raising effect to be achieved by large numbers of sensor pedestals simultaneously. Subjects describe this as a highly novel but not unpleasant sensory experience, something like a scalp massage by a hundred small, wet fingers.

In this preferred embodiment with EEG sponge electrodes, another advantage is that the sensor pedestal feet isolate the sponges from contact with the hair after application is complete. The electrode sponge extends only a few millimeters beyond the pedestal tube. When the positioning network is stable and the radial compression is constant, the majority of the sponge is covered by the flared tube end. Because it is then mostly isolated from hair and air, the sponge focuses its limited electrolyte load on the objective of hydrating the immediate scalp below. This effect maximizes electrical conductance, as well as stable scalp friction, with little or no attention to the individual sensor pedestals during the application procedure.

LIST OF REFERENCE NUMERALS FOR FIG. 1

12—EEG electrode wire
13—electrolyte sponge
14—sensor pedestal tube
15—sensor pedestal collar
16—elastic network thread
17—lock ring for collar and elastic thread
18—flared tube end at foot of pedestal

BRIEF DESCRIPTION OF THE DRAWING

FIG. 1 is a pictorial view of the present invention.

DETAILED DESCRIPTION OF THE INVENTION

FIG. 1 shows a preferred embodiment of the sensor positioning pedestal. The EEG electrode of this preferred embodiment, shown in FIG. 1 in a cutaway view, is a standard silver/silver chloride electrode attached to the amplifier lead wire (12) with solder, with the solder junction coated by epoxy and shrink wrap. The electrode is embedded within a sea sponge (13) soaked in a saline electrolyte.

The electrode and sponge are contained within the sensor pedestal tube (14), an elongate member formed in this embodiment by a clear plastic tube. The sensor pedestal tube is flared at the foot, where the pedestal meets the scalp (18) forming an acute angle at the tip of the flared foot at the intersection of the upper portion of the flared foot and the scalp. The sponge is slit, to cover both sides of the electrode with saline, and it is cut just large enough to make a snug fit in the tube and to extend a few millimeters beyond the tube at the foot (13). Adjusting the protrusion of the sponge from the foot of the sensor pedestal balances two objectives. First, enough sponge protruding insures that the plastic tube does not rest against the scalp. The sponge therefore acts as a comfortable cushion for the radial compression force. Second, not too much sponge protruding insures that after compression most of the sponge is covered by the flared tube end. The electrolyte is therefore kept from drying out.

The sensor pedestal collar (15) is a planar member joined perpendicular to the sensor pedestal tube. It is formed in this embodiment by a hexagonal or pentagonal flat piece of plastic with a hole in the center through which the sensor pedestal tube is fitted. The collar maintains the pedestal in a radial orientation by keeping it perpendicular to the surface of the holding device. The lines of tension in the holding device are directed explicitly in my concurrent invention of the geodesic sensor positioning tension network. They are organized more haphazardly in conventional elastic caps. In either case, the surface of the holding device is formed because the tension is balanced in multiple opposing directions. When the sensor pedestal collar is attached to that surface, such as by sewing the elastic threads of the tension structure network to the perimeter of the collar, any tilt of the collar out of the plane of the tension surface has the effect of increasing the tension (in the direction in which the tilt occurs). The lines of tension in an elastic holding device therefore act to oppose any tilting of the collar from the plane of the surface of the device. When the collar is attached perpendicular to the sensor pedestal tube, the balanced lines of tension thereby maintain the sensor pedestal tube in a surface-perpendicular, and thus head-radial, orientation.

In this embodiment the sensor pedestal collar is fixed to the tube by friction. Another embodiment would be a threaded fitting. In either case, an adjustable fitting of collar to tube allows the distance between collar (and thus the holding device) and scalp to be varied. For example, the temples of the skull are relatively flat areas, causing the radial compression applied by the geodesic tension network to the sensor pedestals at the center of the temples to be attenuated. In this preferred embodiment, therefore, longer collar-to-scalp distances for these temple-center pedestals are implemented to insure that a generally spherical geodesic structure, and thus an even distribution of radial compression, is maintained throughout the tension structure network.

In practice, frequent adjustment of the collars of a dense sensor array is not convenient. However, it is useful to have nets with different sensor pedestal collar-to-scalp distances on hand. For subjects with thin or fine hair, having the net close to the scalp improves stability. For subjects with thick or extensive hair, creating a large hair zone below the holding device structure is a major advantage of this invention.

In this embodiment, the elastic thread (16) is sewn through the holes in the collar, under the bottom surface of the collar, then up through an opposing hole to go toward the next vertex. The lock ring for collar and net thread (17) is a short section of flexible plastic tubing that fits snugly around the pedestal tube. It not only prevents the collar from travelling down the tube (in the direction of the radial compression force); it locks the elastic thread as well. During the sewing of the net, a space is maintained between the collar and the lock ring, so that the thread passes through the collar holes fairly easily. This allows the pedestals to move within the net structure, such that at the completion of sewing the entire structure can be adjusted. The tension on the geodesic lines is adjusted until each sensor pedestal foot is placed at the correct position (these positions are provided by a construction template). When the adjustment is successful, a pliers tool is used to cinch each lock ring up against the collar, thereby fixing each thread line between lock ring and collar at the correct tension.

SUMMARY, RAMIFICATIONS, AND SCOPE

As the network of multiple sensor pedestals is applied to the head, the design of the sensor pedestal keeps it oriented radially to the head as the surface of the holding device conforms to the shape of the head. With this radial orientation held securely, the sensor pedestal is able to keep the holding device at a measured distance from the head. This achieves the object of having only the sensor pedestal itself extend through the hair. The application procedure is designed to allow the flared end of each sensor pedestal foot to position itself below the hair, against the scalp. Small back-and-forth movements of the array of sensors during application cause the flared feet to rake the hair up above the flare, thus placing the sensor surface, which is a sponge electrode in the preferred embodiment, directly on the scalp.

While my above description contains many specificities, these should not be construed as limitations on the scope of the invention, but rather as an exemplification of one preferred embodiment thereof. Many other variations are possible. For example, instead of being incorporated into the tension structure network of my concurrent invention, the sensor pedestal could be used to improve the performance of a conventional elastic cap design. The pedestal collar simply needs to be attached to the elastic fabric of the cap, such that the collar is maintained in the plane of the fabric, and the radial orientation of the pedestal is then insured.

For another example, the advantages of the invention may not be limited to an embodiment with EEG electrodes. New technologies may require other sensors, such as those detecting the brain's magnetic fields or those detecting the radiologic emissions from imaging isotopes, to be positioned against the head. The advantage of avoiding contact with the hair to improve friction against the scalp would accrue to any array of measurement sensors.

Accordingly, the scope of the invention should be determined not by the embodiments illustrated, but by the appended claims and their legal equivalents.

I claim:

1. An apparatus for positioning a sensor against a human head comprising:
   (a) an elongate tubular member with a flared end at a foot of said elongate member;
   (b) an electrode within said tubular member and adapted at the foot of the tubular member for electrical connection to the scalp of the human head; and
   (c) means for positioning said elongate member perpendicular to the surface of the scalp such that the flared end is adjacent to the surface of the scalp.

2. The apparatus of claim 1 further including an absorbent material soaked in a saline electrolyte encasing said electrode within said elongate tubular member.

* * * * *